(12) United States Patent
Roberts

(10) Patent No.: US 8,609,156 B2
(45) Date of Patent: Dec. 17, 2013

(54) COMPOSITIONS AND METHODS OF TREATMENT THAT INCLUDE PLANT EXTRACTS

(75) Inventor: Stephen Charles Roberts, Minnetonka, MN (US)

(73) Assignee: Protanza Corporation, St. Louis Park, MN (US)

( * ) Notice: Subject to any disclaimer, the term of this patent is extended or adjusted under 35 U.S.C. 154(b) by 0 days.

(21) Appl. No.: 13/500,504

(22) PCT Filed: Oct. 5, 2010

(86) PCT No.: PCT/US2010/051472
§ 371 (c)(1),
(2), (4) Date: Jun. 28, 2012

(87) PCT Pub. No.: WO2011/044122
PCT Pub. Date: Apr. 14, 2011

(65) Prior Publication Data
US 2012/0269912 A1    Oct. 25, 2012

Related U.S. Application Data

(60) Provisional application No. 61/278,148, filed on Oct. 5, 2009, provisional application No. 61/280,739, filed on Nov. 9, 2009.

(51) Int. Cl.
*A01N 65/00* (2009.01)

(52) U.S. Cl.
USPC ........................................................ 424/725

(58) Field of Classification Search
None
See application file for complete search history.

(56) References Cited

U.S. PATENT DOCUMENTS

| 6,086,886 A | 7/2000 | Guo |
| 2002/0034555 A1 | 3/2002 | Gelber et al. |
| 2006/0222722 A1 | 10/2006 | Roberts et al. |

FOREIGN PATENT DOCUMENTS

| WO | WO-2006106350 A1 | 10/2006 |
| WO | WO-2011044122 A1 | 4/2011 |

OTHER PUBLICATIONS

International Application Serial No. PCT/US2010/051472, Search Report and Written Opinion mailed Mar. 29, 2011, 10 pgs.

*Primary Examiner* — Michael Meller
(74) *Attorney, Agent, or Firm* — Schwegman, Lundberg & Woessner, P.A.

(57) ABSTRACT

The present invention provides for a pharmaceutical composition that provides for the symptomatic relief to an animal (e.g., mammal, such as a human) afflicted with inflammation. The pharmaceutical composition includes a pharmaceutically acceptable carrier and at least two of: (a) sunflower extract, (b) rhubarb root extract, (c) milk thistle extract, (d) dandelion extract, (e) feverfew extract, and (f) ginger extract. The present invention also provides for a method for providing symptomatic relief to a human afflicted with inflammation. The method includes administering to a patient in need of such symptomatic relief an effective amount of the pharmaceutical composition described herein, for a period of time sufficient to provide symptomatic relief to the human.

1 Claim, No Drawings

COMPOSITIONS AND METHODS OF TREATMENT THAT INCLUDE PLANT EXTRACTS

RELATED APPLICATIONS

This application is a U.S. National Stage Filing under 35 U.S.C. 371 from and claims the benefit of priority under 35 U.S.C. §120 to International Patent Application No. PCT/US2010/051472, filed on Oct. 5, 2010, and published on Apr. 14, 2011, as WO 2011/044122, which claims the benefit of priority under 35 U.S.C. Section 119(e) to both U.S. Provisional Patent Application Ser. No. 61/278,148, filed Oct. 5, 2009, and to U.S. Provisional Patent Application Ser. No. 61/280,739, filed Nov. 9, 2009, which are all incorporated herein by reference in their entirety.

BACKGROUND

Fibromyalgia is a disease characterized by widespread musculoskeletal pain and tenderness on palpation at so called tenderpoints. The disease is diagnosed according to criteria as defined by the American College of Rheumatology (ACR) [see Arthritis and Rheumatism, Vol. 33, No. 2, pages 160-172, 1990]. In addition to pain symptoms, in the majority of fibromyalgia patients a variety of functional symptoms such as headache, insomnia, irritable bowel syndrome, sicca symptoms, increased sweating, dizziness, tremor, dyspnoea, arrhythmias, paraesthesias, headache/migraine, fatigue, psychopathological disorders and others occur. Therefore, the medical approaches towards management of fibromyalgia should not exclusively aim at relief of pain symptoms but also aim at improvements in functional symptoms.

Currently, there is a need for compositions that provide for the symptomatic relief from fibromyalgia and other diseases and disorders, believed by some within the medical community, to be related to inflammation, e.g., arthritis, osteoarthritis, herniated cervical disc, chronic fatigue syndrome, gout, rheumatoid arthritis, lupus, multiple sclerosis, neuropathic pain, irritable bowel syndrome (IBS), depression, anxiety, Sjögren's Syndrome, and Ehlers-Danlos Syndrome. These diseases and disorders can have symptoms associated with inflammation, that include, e.g., diffuse pain, jaw or facial pain, back or neck pain, muscle pain, joint pain, arthritis pain, osteoarthritis pain, pelvic pain, chest pain, neuropathic pain, vulvodynia, urethral pain, weakness, fatigue, chronic fatigue, dizziness, paresthesia, impaired cognition, sleep disturbance, joint stiffness, tendonitis, hypersensitivity to cold, hypersensitivity to sensory stimuli, photophobia, phonophobia, osmophobia, allodynia, hyperalgesia, and headache.

SUMMARY

The present invention provides for a pharmaceutical composition that provides for the symptomatic relief to an animal (e.g., mammal such as a human) afflicted with inflammation. The symptomatic relief can include alleviating the symptom of a disease or condition. Such alleviation can include lessening the intensity of the symptom, lessening the duration of the symptom, and/or lessening the frequency of the symptom.

The symptom associated with inflammation can include at least one of psoriasis, diffuse pain, jaw or facial pain, back or neck pain, muscle pain, joint pain, arthritis pain, osteoarthritis pain, pelvic pain, chest pain, neuropathic pain, vulvodynia, urethral pain, weakness, fatigue, chronic fatigue, dizziness, paresthesia, impaired cognition, sleep disturbance, joint stiffness, tendonitis, hypersensitivity to cold, hypersensitivity to sensory stimuli, photophobia, phonophobia, osmophobia, allodynia, hyperalgesia, and headache.

The inflammation can be associated with at least one of arthritis, fibromyalgia, osteoarthritis, herniated cervical disc, chronic fatigue syndrome, gout, rheumatoid arthritis, lupus, multiple sclerosis, neuropathic pain, irritable bowel syndrome (IBS), depression, anxiety, Sjögren's Syndrome, and Ehlers-Danlos Syndrome.

The pharmaceutical composition can be in an oral dosage form, e.g., oral tablet, lozenge or troche, having a relatively large mass, e.g., at least about 0.5 gram, at least about 0.750 gram or at least about 1 gram.

The pharmaceutical composition includes a pharmaceutically acceptable carrier and at least two of: (a) sunflower extract, (b) rhubarb root extract, (c) milk thistle extract, (d) dandelion extract, (e) feverfew extract, and (f) ginger extract. In specific embodiments, the pharmaceutical composition can include a pharmaceutically acceptable carrier and at least three of (a)-(f), at least four of (a)-(f), at least five of (a)-(f), or each and every one of (a)-(f).

When present, the sunflower extract can be present in any suitable, effective and appropriate amount, e.g., in about 1 wt. % to about 10 wt. % of the composition. When present, the rhubarb root extract can be present in any suitable, effective and appropriate amount, e.g., in about 0.5 wt. % to about 5 wt. % of the composition. When present, the milk thistle extract can be present in any suitable, effective and appropriate amount, e.g., in about 0.5 wt. % to about 5 wt. % of the composition. When present, the dandelion extract can be present in any suitable, effective and appropriate amount, e.g., in about 0.1 wt. % to about 3 wt. % of the composition. When present, the feverfew extract can be present in any suitable, effective and appropriate amount, e.g., in about 0.1 wt. % to about 3 wt. % of the composition. When present, the ginger extract can be present in any suitable, effective and appropriate amount, e.g., in about 0.1 wt. % to about 3 wt. % of the composition.

The pharmaceutical composition can optionally further include lemon extract. When present, the lemon extract can be present in any suitable, effective and appropriate amount, e.g., in about 1 wt. % to about 15 wt. % of the composition.

The pharmaceutical composition can optionally further include peppermint extract. When present, the peppermint extract can be present in any suitable, effective and appropriate amount, e.g., in about 0.1 wt. % to about 5 wt. % of the composition.

The pharmaceutical composition can optionally further include any one or more of the following substances that, when present, can be present in any suitable, effective and appropriate amount: turmeric extract, rebiana, cellulose, corn starch, citric acid, dextrose, and magnesium stearate.

The pharmaceutical composition can optionally further include any one or more of the following substances that, when present, can be present in any suitable, effective and appropriate amount: an adsorbent, suspending agent, diluent, disintegrant, glidant, binder, acidifying agent, basifying agent, antioxidant, buffering agent, chelating agent, flavor enhancer, tonicity agent, sweetening agent, lubricant, flavoring agent, coloring agent, dye, and penetration enhancer.

In a particularly specific embodiment of the invention, the pharmaceutical composition can include: (a) lemon extract, (b) sunflower extract, (c) rhubarb root extract, (d) milk thistle extract, (e) dandelion extract, (f) feverfew extract, (g) ginger extract, (h) cellulose, (i) citric acid, (j) corn starch, (k) dextrose, (l) magnesium stearate, (m) peppermint extract, (n) rebiana, and (o) turmeric extract.

The present invention also provides for a method for providing symptomatic relief to a human afflicted with inflammation. The method includes administering to a patient in need of such symptomatic relief an effective amount of the pharmaceutical composition described herein, for a period of time sufficient to provide symptomatic relief to the human.

The present invention also provides for the compositions described herein, for use as a medicament. The present invention also provides for the compositions described herein, for use in providing symptomatic relief to a human afflicted with inflammation. The present invention also provides for the use of the compositions described herein to prepare a medicament for providing symptomatic relief to a human afflicted with inflammation.

The pharmaceutical composition can be systemically administered, e.g., administered transmucosally via the mucosal membrane of the mouth. The administration can occur over an extended period of time, e.g., from about 2 minutes to about 30 minutes. The pharmaceutical composition can be administered one or more times (e.g., 1, 2, 3, 4 or 5) per day. Additionally, the composition can be administered over an extended period of time, e.g., at least about 1 week.

DETAILED DESCRIPTION

References in the specification to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

Combination of Extracts

In one embodiment, the pharmaceutical composition can include a pharmaceutically acceptable carrier and at least two of: (a) sunflower extract, (b) rhubarb root extract, (c) milk thistle extract, (d) dandelion extract, (e) feverfew extract, and (f) ginger extract. In such an embodiment, the pharmaceutical composition can include at least: AB, AC, AD, AE, AF, BC, BD, BE, BF, CD, CE, CF, DE, DF, or EF; wherein A-F represent components (a)-(f), respectively. This can be illustrated with the following matrix, wherein italicized text indicates that the combination is not contemplated, because it is either duplicative of another combination (e.g., AB and BA), or is not a two component combination (e.g., AA or BB):

Pharmaceutical Composition

Combination of Two Extracts

|  | sunflower extract (A) | rhubarb root extract (B) | milk thistle extract (C) | dandelion extract (D) | feverfew extract (E) | ginger extract (F) |
|---|---|---|---|---|---|---|
| sunflower extract (A) | *AA* Not a two-component system | AB | AC | AD | AE | AF |
| rhubarb root extract (B) | *BA* Duplicative of AB | *BB* Not a two-component system | BC | BD | BE | BF |
| milk thistle extract (C) | *CA* Duplicative of AC | *CB* Duplicative of BC | *CC* Not a two-component system | CD | CE | CF |
| dandelion extract (D) | *DA* Duplicative of AD | *DB* Duplicative of BD | *DC* Duplicative of CD | *DD* Not a two-component system | DE | DF |
| feverfew extract (E) | *EA* Duplicative of AE | *EB* Duplicative of BE | *EC* Duplicative of CE | *ED* Duplicative of DE | *EE* Not a two-component system | EF |
| ginger extract (F) | *FA* Duplicative of AF | *FB* Duplicative of BF | *FC* Duplicative of CF | *FD* Duplicative of DF | *FE* Duplicative of EF | *FF* Not a two-component system |

In another embodiment, the pharmaceutical composition can include a pharmaceutically acceptable carrier and at least three of: (a) sunflower extract, (b) rhubarb root extract, (c) milk thistle extract, (d) dandelion extract, (e) feverfew extract, and (f) ginger extract. In such an embodiment, the pharmaceutical composition can include at least: ABC, ABD, ABE, ABF, ACD, ACE, ACF, ADE, ADF, AEF, BCD, BCE, BCF, BDE, BDF, BEF, CDE, CDF, CEF, or DEF; wherein A-F represent components (a)-(f), respectively.

In another embodiment, the pharmaceutical composition can include a pharmaceutically acceptable carrier and at least four of: (a) sunflower extract, (b) rhubarb root extract, (c) milk thistle extract, (d) dandelion extract, (e) feverfew extract, and (f) ginger extract. In such an embodiment, the pharmaceutical composition can include at least: ABCD, ABCE, ABCF, ABDE, ABDF, ABEF, ACDE, ACDF, ADEF, BCDE, BCDF, or CDEF, wherein A-F represent components (a)-(f), respectively.

In another embodiment, the pharmaceutical composition can include a pharmaceutically acceptable carrier and at least five of: (a) sunflower extract, (b) rhubarb root extract, (c) milk thistle extract, (d) dandelion extract, (e) feverfew extract, and (f) ginger extract. In such an embodiment, the pharmaceutical composition can include at least: ABCDE, ABCDF, ABDEF, ACDEF, ABCEF, or BCDEF, wherein A-F represent components (a)-(f), respectively.

In another embodiment, the pharmaceutical composition can include a pharmaceutically acceptable carrier and each and every one of (a)-(f): (a) sunflower extract, (b) rhubarb root extract, (c) milk thistle extract, (d) dandelion extract, (e) feverfew extract, and (f) ginger extract. In such an embodiment, the pharmaceutical composition can include ABCDEF, wherein A-F represent components (a)-(f), respectively.

The present invention relates to a pharmaceutical composition that provides for the symptomatic relief to a human afflicted with inflammation, and to methods of providing for the symptomatic relief to a human afflicted with inflammation. When describing the pharmaceutical composition that provides for the symptomatic relief to a human afflicted with inflammation, and/or to methods of providing for the symptomatic relief to a human afflicted with inflammation the following terms have the following meanings, unless otherwise indicated.

Sunflower Extract

The term "sunflower extract" refers to material derived from a diversity of species and subspecies corresponding with the common name "sunflower" and may be incorporated into the composition of the present invention in a variety of different forms. Those different forms include but are not limited to sunflower extracts, one or more compounds isolated from and naturally occurring in sunflowers, sunflower powder, and mixtures thereof. The sunflower can be *Helianthus annuus*. The part of the plant can be, for example, the whole seed of the mature plant or a part of the seed of the mature plant. The sunflower extract can be a powdered extract derived exclusively from the whole seeds of the mature plant.

When present, the sunflower extract can be present in the composition described herein, in any suitable, effective and appropriate amount. For example, when present, the sunflower extract can be present in about 0.25 wt. % to about 20 wt. % of the composition, in about 0.5 wt. % to about 10 wt. % of the composition, or in about 1 wt. % to about 5 wt. % of the composition. In one specific embodiment, the sunflower extract is present in about 2.5 wt. % of the composition.

Rhubarb Root Extract

The term "rhubarb root extract" refers to a material derived from a diversity of species and subspecies corresponding with the common name "rhubarb" and may be incorporated into the composition of the present invention in a variety of different forms. Those different forms include but are not limited to rhubarb root extracts, one or more compounds isolated from and naturally occurring in rhubarb root, rhubarb root powder, and mixtures thereof. The rhubarb can be *Rheum rhabarbarum*. Another specific rhubarb is *Rheum palmatum*. The plant part can be, for example, the whole root or rhizome of the plant. The form can be a dry powder derived from the root or rhizome of the plant.

When present, the rhubarb root extract can be present in the composition described herein, in any suitable, effective and appropriate amount. For example, when present, the rhubarb root extract can be present in about 0.1 wt. % to about 10 wt. % of the composition, in about 0.3 wt. % to about 5 wt. % of the composition, or in about 0.6 wt. % to about 2.5 wt. % of the composition. In one specific embodiment, the rhubarb root extract is present in about 1.25 wt. % of the composition.

Milk Thistle Extract

The term "milk thistle extract" refers to a material derived from a diversity of species and subspecies corresponding with the common name "milk thistle" and may be incorporated into the composition of the present invention in a variety of different forms. Those different forms include but are not limited to milk thistle extracts, one or more compounds isolated from and naturally occurring in milk thistle, milk thistle powder, and mixtures thereof. The milk thistle can be of genus *Silybum*, e.g., *Silybum marianum*. The plant can be, for example, the fruit or seed of the plant. The form can be a dry powder derived from the fruit or seed of the plant.

When present, the milk thistle extract can be present in the composition described herein, in any suitable, effective and appropriate amount. For example, when present, the milk thistle extract can be present in about 0.1 wt. % to about 10 wt. % of the composition, in about 0.3 wt. % to about 5 wt. % of the composition, or in about 0.6 wt. % to about 2.5 wt. % of the composition. In one specific embodiment, the milk thistle extract is present in about 1.25 wt. % of the composition.

Dandelion Extract

The term "dandelion extract" refers to material derived from a diversity of species and subspecies corresponding with the common name "dandelion" and may be incorporated into the composition of the present invention in a variety of different forms. Those different forms include but are not limited to dandelion extracts, one or more compounds isolated from and naturally occurring in dandelion, dandelion powder, and mixtures thereof. The dandelion can be *Taraxacum officinale*. The plant part can be, for example, the whole plant. The form can be a dry powdered extract derived from the whole plant.

When present, the dandelion extract can be present in the composition described herein, in any suitable, effective and appropriate amount. For example, when present, the dandelion extract can be present in about 0.1 wt. % to about 6 wt. % of the composition, in about 0.2 wt. % to about 3 wt. % of the composition, or in about 0.3 wt. % to about 1.50 wt. % of the composition. In one specific embodiment, the dandelion extract is present in about 0.75 wt. % of the composition.

Feverfew Extract

The term "feverfew extract" refers to material derived from a diversity of species and subspecies corresponding with the common name "feverfew" and may be incorporated into the composition of the present invention in a variety of different forms. Those different forms include but are not limited to feverfew extracts, one or more compounds isolated from and naturally occurring in feverfew including parthenolide, feverfew powder, and mixtures thereof. The feverfew can be *Tanacetum parthenium*. The plant parts can be, for example, the leaves and flowers. The form can be a dry powdered extract derived exclusively from the leaves and flowers.

When present, the feverfew extract can be present in the composition described herein, in any suitable, effective and appropriate amount. For example, when present, the feverfew extract can be present in about 0.01 wt. % to about 1.0 wt. % of the composition, in about 0.03 wt. % to about 0.4 wt. % of the composition, or in about 0.05 wt. % to about 0.2 wt. % of the composition. In one specific embodiment, the feverfew extract is present in about 0.1 wt. % of the composition.

Ginger Extract

The term "ginger extract" refers to material derived from a diversity of species and subspecies corresponding with the common name "ginger" and may be incorporated into the composition of the present invention in a variety of different forms. Those different forms include but are not limited to ginger extracts, one or more compounds isolated from and naturally occurring in ginger such as the gingerols, ginger powder, and mixtures thereof. The ginger can be *Zingiber officinale*. The plant part can be, for example, the root or rhizome. The form can be a dry powdered extract derived exclusively from the root or rhizome.

When present, the ginger extract can be present in the composition described herein, in any suitable, effective and appropriate amount. For example, when present, the ginger extract can be present in about 0.05 wt. % to about 4.0 wt. % of the composition, in about 0.1 wt. % to about 2.0 wt. % of the composition, or in about 0.25 wt. % to about 1.0 wt. % of the composition. In one specific embodiment, the ginger extract is present in about 0.5 wt. % of the composition.

Lemon Extract

The term "lemon extract" refers to material derived from a diversity of species and subspecies corresponding with the common name "lemon" and may be incorporated into the composition of the present invention in a variety of different forms. Those different forms include but are not limited to lemon extracts, one or more compounds isolated from and naturally occurring in lemon, lemon powder, and mixtures thereof. The lemon can be *Citrus limon*. The plant part can be, for example, the entire mature fruit. The form can be a dry powdered extract derived exclusively from the entire mature fruit.

When present, the lemon extract can be present in the composition described herein, in any suitable, effective and appropriate amount. For example, when present, the lemon extract can be present in about 0.6 wt. % to about 40 wt. % of the composition, in about 1.25 wt. % to about 20 wt. % of the composition, or in about 2.5 wt. % to about 10 wt. % of the composition. In one specific embodiment, the lemon extract is present in about 5 wt. % of the composition.

Peppermint Extract

The term "peppermint extract" refers to material derived from a diversity of species and subspecies corresponding with the common name "peppermint" and may be incorporated into the composition of the present invention in a variety of different forms. Those different forms include but are not limited to peppermint extracts, one or more compounds isolated from and naturally occurring in peppermint, peppermint powder, and mixtures thereof. The peppermint can be *Mentha piperita*. The plant part can be, for example, the leaf. The form can be a dry powdered extract derived exclusively from the leaves of the plant.

When present, the peppermint extract can be present in the composition described herein, in any suitable, effective and appropriate amount. For example, when present, the peppermint extract can be present in about 0.1 wt. % to about 8 wt. % of the composition, in about 0.25 wt. % to about 4 wt. % of the composition, or in about 0.5 wt. % to about 2 wt. % of the composition. In one specific embodiment, the peppermint extract is present in about 1 wt. % of the composition.

Turmeric Extract

The term "turmeric extract" refers to material derived from a diversity of species and subspecies corresponding with the common name "turmeric" and may be incorporated into the composition of the present invention in a variety of different forms. Those different forms include but are not limited to turmeric extracts, one or more compounds isolated from and naturally occurring in turmeric, turmeric powder, and mixtures thereof. The turmeric can be *Curcuma longa*. The plant part can be, for example, the root or rhizome. The form can be a dry powdered extract derived exclusively from the root or rhizome of the plant.

When present, the turmeric extract can be present in the composition described herein, in any suitable, effective and appropriate amount. For example, when present, the turmeric extract can be present in about 0.6 wt. % to about 40 wt. % of the composition, in about 1.3 wt. % to about 20 wt. % of the composition, or in about 2.5 wt. % to about 10 wt. % of the composition. In one specific embodiment, the turmeric extract is present in about 5 wt. % of the composition.

Plant Material or Plant Tissue

As used herein, "plant material" or "plant tissue" refers to a collection of similar cells of a plant, that typically act together to perform a particular function. The term refers to the tissue of any organism of the plant kingdom, as opposed to one of the animal kingdom or of the kingdoms of Fungi, Protista, or Monera. The plant tissue can be any portion or portions of the plant (e.g., bark, roots, leaves, flowers, needles, bulbs, berries, rhizomes, rootstocks, stems, and seeds), as well as the entire plant. The tissues of a plant ("plant tissue") generally fall into three main categories: dermal tissue, ground tissue, and vascular tissue. Dermal tissue refers to the "skin" layer of all plant organs and is responsible for environmental interaction (light passage, gas exchange, pathogen recognition and protection, color display, etc.). Dermal tissue is composed of epidermal cells, closely packed cells that secrete a waxy cuticle that aids in the prevention of water loss. Ground tissue lies between dermal tissue and vascular tissue. The ground tissue comprises the bulk of the primary plant body. Parenchyma, collenchyma, and sclerenchyma cells are common in the ground tissue. In roots, the ground tissue may store sugars or starches to fuel the spring sap flow; in leaves, the ground tissue is the layer responsible for photosynthesis (the mesophyll). Vascular tissue transports food, water, hormones and minerals within the plant. Vascular tissue includes xylem, phloem, parenchyma, and cambium cells.

Seed

As used herein, "seed" refers to a ripened ovule, consisting of an embryo with one or more integuments, or coverings, such as an apple seed, a currant seed, dill seed, or kola nut seed. By germination, most seeds produce a new plant. "Seed" also refers to any small seedlike fruit, though it may consist of a pericarp, or even a calyx, as well as the seed proper, such as a parsnip seed or thistle seed. The seed proper has an outer and an inner coat, and within these the kernel or nucleus. The kernel is either the embryo alone, or the embryo enclosed in the albumen, which is the material for the nourishment of the developing embryo. The scar on a seed, left where the stem parted from it, is called the hilum, and the closed orifice of the ovule, the micropyle.

Root

As used herein, "root" refers to the part of a plant, normally underground, that absorbs nutrients and anchors the plant into the ground and sometimes stores nutrients, as in the case of a rhizome.

Rebiana

The term "rebiana" refers to rebaudioside A, a steviol glycoside which when used as a non-nutritive sweetener is 200 times sweeter than sugar. Rebiana can be derived from stevia leaves by steeping them in water. See, http://en.wikipedia.org/wiki/Rebiana.

Cellulose

The term "cellulose" refers to a polymer illustrated by the chemical structure shown below.

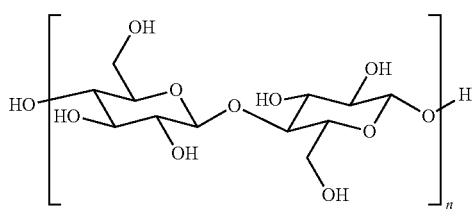

Where n=about 50 to about 5000, or about 125 to about 2000, or about 250 to about 1000. In one specific embodiment, n=about 500.

Cellulose can be used, for example, as an absorbent, a glidant, a suspending agent, a tablet and capsule diluent, a binder, or as a tablet disintegrant. See, Handbook of Pharmaceutical Excipients, 5$^{th}$ Ed., 2006, page 137.

Corn Starch

The term "corn starch" refers to the starch of the corn or maize grain obtained from the endosperm of the corn kernel. See, http://en.wikipedia.org/wiki/Corn_starch.

Citric Acid

The term "citric acid" refers to 2-hydroxypropane-1,2,3-tricarboxylic acid, and is illustrated by the chemical structure shown below.

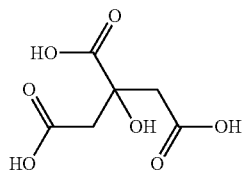 [SMILES: O=C(O)CC(O)(CC(=O)O)C(=O)O]

Citric acid can be used, for example, as an acidifying agent, an antioxidant, a buffering agent, a chelating agent, or a flavor enhancer. Citric acid can be present as a hydrate or an anhydrate. See, Handbook of Pharmaceutical Excipients, 5$^{th}$ Ed., 2006, page 185.

Dextrose

The term "dextrose" refers to D-(+)-glucose, and is illustrated by the chemical structural shown below.

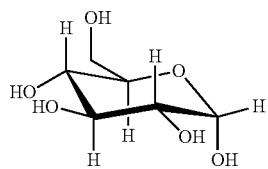

Dextrose can be used, for example, as a tablet and capsule diluent, a binder, a therapeutic agent, a tonicity agent, or as a sweetening agent. Dextrose can be present as a hydrate or an anhydrate. Dextrose can be used in solutions to adjust tonicity and as a sweetening agent. The mildly reducing properties of dextrose can be used when tableting to improve the stability of active materials that are sensitive to oxidation. See, Handbook of Pharmaceutical Excipients, 5$^{th}$ Ed., 2006, page 231.

Magnesium Stearate

The term "magnesium stearate" refers to the magnesium salt of octadecanoic acid. It can be used as, for example, a tablet and capsule lubricant. It can be used in, for example, about 0.1 wt. % to about 10.0 wt. %. Alternatively, it can be used in, for example, about 0.25% wt. % to about 5.0% wt. %. See, Handbook of Pharmaceutical Excipients, 5$^{th}$ Ed., 2006, page 430.

Adsorbent

The term "adsorbent" refers to a material to which other materials will stick.

Suspending Agent

The term "suspending agent" refers to a compound or substance that increases the ability of suspension to remain as such and to lessen settling. It includes compounds or substances that can increase the viscosity of a solution.

Diluent

The term "diluent" refers to a compound or substance used to make a solution or solid mixture more dilute. It can be added to a tablet to increase bulk. Examples can include dicalcium phosphate, calcium sulfate, lactose, cellulose, kaolin, mannitol, sodium chloride, dry starch, powdered sugar, and other substances known to one of skill in the art. See, Mosby's Medical, Nursing, & Allied Health Dictionary, 5$^{th}$ Ed., 1998, definition of "buffer", page 492. See also, Remington's Pharmaceutical Sciences, 18$^{th}$ Ed., 1990, page 1635, first column last partial paragraph to second column third full paragraph.

Disintegrant

The term "disintegrant" refers to a compound or substance used to cause a tablet or other form to break up or disintegrate when exposed to a particular solvent environment, for example an aqueous environment. Examples of disintegrants can include starches, clays, celluloses, gums, crosslinked polymers, and other substances known to one of skill in the art. See, Remington's Pharmaceutical Sciences, 18$^{th}$ Ed., 1990, page 1452, second column, second to last full paragraph, and page 1637, first column fourth full paragraph to second column fifth full paragraph.

Glidant

The term "glidant" refers to a substance which improves the flow characteristics of a powder mixture. Examples can include colloidal silicon dioxide, talc, and other substances known to one of skill in the art. See, Remington's Pharmaceutical Sciences, 18$^{th}$ Ed., 1990, page 1637, first column, second and third full paragraphs.

Binder

The term "binder" refers to a compound or substance used to give a powder or other substance bulk, allowing an acceptably-sized tablet or other form to be produced. They also can contribute cohesive properties to, and adjust the hardness of the tablet or other form. See, Remington's Pharmaceutical Sciences, 18$^{th}$ Ed., 1990, page 1452, fourth full paragraph, and page 1635, second column, last full paragraph.

Acidifying Agent

The term "acidifying agent" refers to a compound or substance used to decrease the pH of a material or the environment of use of that material.

Basifying Agent

The term "basifying agent" refers to a compound or substance used to increase the pH of a material or the environment of use of that material.

Antioxidant

The term "antioxidant" refers to a compound or substance that inhibits or retard oxidation of a substance or mixture to which it is added. See, Mosby's Medical, Nursing, & Allied Health Dictionary, 5$^{th}$ Ed., 1998, page 107.

Buffering Agent

The term "buffering agent" refers to a compound or substance used to minimize significant changes of pH. The control of pH can occur in the substance or mixture to which it is added, or in the environment in which the final substance or mixture is to be used. See, Mosby's Medical, Nursing, & Allied Health Dictionary, 5$^{th}$ Ed., a 1998, definition of "buffer", page 235.

Chelating Agent

The term "chelating agent" refers to a compound or substance that promotes a chemical reaction in which there is a combination with a metal or other atom to form a sometimes ring-shaped molecular complex in which the metal or atom is bound. Some types of chelating agents can be specific to various types of metals or other atoms.

Tonicity Agent

The term "tonicity agent" refers to a compound or substance that can be used to adjust the composition of the formulation to the desired isotonic range. Some examples include glycerin, mannitol, sorbitol, sodium chloride, and other electrolytes.

Sweetening Agent

The term "sweetening agent" refers to a compound or substance used to increase or enhance the sweetness of a compound or substance to which it is added. See, Remington's Pharmaceutical Sciences, 18$^{th}$ Ed., 1990, page 1638, second column, first full paragraph.

Lubricant

The term "lubricant" refers to a compound or substance used to enhance the flow of a powder and to prevent sticking of a tablet in a die machine after a tablet or other form is compressed. Examples can include talc, magnesium stearate, calcium stearate, stearic acid, hydrogenated vegetable oils, polyethylene glycol, and other substances known to one of skill in the art. See, Remington's Pharmaceutical Sciences, 18$^{th}$ Ed., 1990, page 1452, second column, last full paragraph, and page 1636, second column, third full paragraph to page 1637, first column, first full paragraph.

Flavoring Agent or Flavor Enhancer

The terms "flavoring agent" or "flavor enhancer" refer to a compound or substance added to a substance or mixture to generate or enhance flavor. Examples can include sweeteners, fruit flavors, or other compounds or substances known to one of skill in the art. See, Remington's Pharmaceutical Sciences, 18$^{th}$ Ed., 1990, page 1638, second column, first full paragraph.

Coloring Agent or Dye

The term "coloring agent" or "dye" refers to a compound or substance added to a substance or mixture to control or generate the color of the substance or mixture. See, Remington's Pharmaceutical Sciences, 18$^{th}$ Ed., 1990, page 1637, last partial paragraph to page 1638, second column first partial paragraph.

Penetration Enhancer

The term "penetration enhancer" refers to a compound or substance that increases the ability of another substance to be absorbed into or through the skin or mucous membrane.

Oral Administration

The term "oral administration" refers to the administration of a tablet, capsule, an elixir, or a solution or other liquid form of medication by mouth. See, Mosby's Medical, Nursing, & Allied Health Dictionary, 5$^{th}$ Ed., a 1998, definition of "troche" at page 1657.

Transmucosal Administration

The term "transmucosal administration" refers to administration of a substance, such as a drug, through the mucous membranes.

Oral Tablet

The term "oral tablet" refers to a solid dosage form of medication that is intended to be swallowed or dissolved in the mouth, chewed, or dissolved in liquid before swallowing. It can be compressed or molded in its manufacture, and it can be of almost any size, shape, weight, and color. See, Mosby's Medical, Nursing, & Allied Health Dictionary, 5$^{th}$ Ed., 1998, definition of "tablet" at page 1584.

Lozenge or Troche

The terms "lozenge" or "troche" refer to a tablet containing a medicinal agent, which dissolved in the mouth, releasing the agent. The lozenge or troche can contain other ingredients including flavors, for example sweetener or fruit flavor. See, Mosby's Medical, Nursing, & Allied Health Dictionary, 5$^{th}$ Ed., 1998, definition of "troche" at page 1657.

Inflammation

The term "inflammation" refers to an immunological response to injury, infection, allergy, trauma or other insult, typically marked by increases in regional blood flow, immigration of white blood cells, and release of chemical agents. Inflammation is one mechanism the body uses to protect itself from invasion by foreign organisms and to repair tissue damage. Some of its clinical hallmarks are redness, heat, swelling, pain, and loss of function of a body part. Systemically, inflammation may produce fevers, joint and muscle pains, organ dysfunction, and malaise. See, Taber's Cyclopedic Medical Dictionary, 19$^{th}$ Ed., 2001, page 1048. See also, Mosby's Medical, Nursing, & Allied Health Dictionary, 5$^{th}$ Ed., 1998, definition of "inflammation" at page 1186.

Symptomatic Relief

The term "symptomatic relief" refers to alleviating the symptom of a disease or condition. Such alleviation can include lessening the intensity of the symptom, lessening the duration of the symptom, and/or lessening the frequency of the symptom.

Administration is Systemic

The term "administration is systemic" refers to administration via oral, parenteral, or transmucosal routes to be absorbed into the circulation for treatment of a health problem. Remedies or medications administered locally or regionally can be to some degree absorbed systemically. Local administration of medication can have various local effects, even when the overall intent is to treat the entire body. See, Mosby's Medical, Nursing, & Allied Health Dictionary, 5th Ed., 1998, definition of "systemic remedy" at page 1583. In specific embodiments, the systemic administration occurs via an oral route.

Mucosal Membrane of the Mouth

The term "mucosal membrane of the mouth" refers to the mucous membrane lining the oral cavity and described by its location on the gingival, hard palate, soft palate, cheek, vestibule, lip, tongue, and pharyngeal area. See, Taber's Cyclopedic Medical Dictionary, 19$^{th}$ Ed., 2001, page 1329.

Pain

The term "pain" refers to an unpleasant sensory and emotional experience arising from actual or potential tissue damage or described in terms of such damage. Pain can include not only the perception of an uncomfortable stimulus but also the response to that perception. See, Taber's Cyclopedic Medical Dictionary, 19$^{th}$ Ed., 2001, page 1487. See also, Mosby's Medical, Nursing, & Allied Health Dictionary, 5$^{th}$ Ed., 1998, definition of "pain" at page 1186. The terms "jaw or facial pain," "back or neck pain," "muscle pain," "joint pain," "pelvic pain," "chest pain," "urethral pain" refers to pain in the respective part of the body.

Diffuse Pain

The term "diffuse pain" refers to pain that is poorly localized or dilute. See, Mosby's Medical, Nursing, & Allied Health Dictionary, 5$^{th}$ Ed., 1998, definition of "pain" at page 1186.

Arthritis Pain

The term "arthritis pain" refers to pain caused by arthritis.

Osteoarthritis Pain

The term "osteoarthritis pain" refers to pain caused by osteoarthritis.

Neuropathic Pain

The term "neuropathic pain" refers to pain that originates in nerves themselves rather than in other damaged organs that are innervated by them. A hallmark of neuropathic pain is its localization to specific dermatomes or nerve distributions. Examples can include but are not limited to the pain of shingles (herpes zoster), diabetic neuropathy, radiculopathy, and phantom limb pain.

Vulvodynia

The term "vulvodynia" refers to vulvar pain. See, Taber's Cyclopedic Medical Dictionary, 19th Ed., 2001, page 2252.

Weakness

The term "weakness" refers to a lack of strength as compared to what a patient feels is normal. See, Taber's Cyclopedic Medical Dictionary, 19th Ed., 2001, page 2258.

Fatigue

The term "fatigue" refers to a sense of exhaustion and decreased capacity for physical and mental work at the usual level. See, Taber's Cyclopedic Medical Dictionary, 19th Ed., 2001, page 747.

Chronic Fatigue

The term "chronic fatigue" refers to fatigue of long duration; fatigue showing little change or of slow progression. See, Taber's Cyclopedic Medical Dictionary, 19th Ed., 2001, definition of "chronic", page 402.

Dizziness

The term "dizziness" refers to lightheadedness, unsteadiness, loss of spatial orientation, or loss of balance. It can also refer to generalized weakness, faintness, or presyncope. See, Taber's Cyclopedic Medical Dictionary, 19th Ed., 2001, page 599.

Paresthesia

The term "paresthesia" refers to an abnormal or unpleasant sensation that results from injury to one or more nerves, often described by patients as, for example, numbness or as a prickly, stinging, or burning feeling. See, Taber's Cyclopedic Medical Dictionary, 19th Ed., 2001, page 1519.

Impaired Cognition

The term "impaired cognition" refers to impairment of mental processes such as knowing, thinking, comprehending, learning, understanding, remembering, reasoning, and judging. See, Mosby's Medical, Nursing, & Allied Health Dictionary, 5th Ed., a 1998, definition of "cognition" and "cognitive" at page 361.

Sleep Disturbance

The term "sleep disturbance" refers to a condition that interrupts or disrupts the sleep time, and can sometimes cause discomfort or interference with a desired life-style. See, Mosby's Medical, Nursing, & Allied Health Dictionary, 5th Ed., 1998, definition of "sleep pattern disturbance" and "sleep" at page 1503.

Joint Stiffness

The term "joint stiffness" refers a rigid, inflexible, or sore joint, as may be caused, for example, by arthritis or other rheumatic disorders. See, Mosby's Medical, Nursing, & Allied Health Dictionary, 5th Ed., 1998, definition of "stiff joint", page 1543.

Tendonitis

The term "tendonitis" refers to inflammation of a tendon. See, Taber's Cyclopedic Medical Dictionary, 19th Ed., 2001, page 2059.

Hypersensitivity

The term "hypersensitivity" refers to an excessive ability to perceive or feel. The terms "hypersensitivity to cold" or "hypersensitivity to sensory stimuli" refer to excessive ability to perceive or feel cold, or sensory stimuli, respectively. See, Mosby's Medical, Nursing, & Allied Health Dictionary, 5th Ed., 1998, page 794.

Photophobia

The term "photophobia" refers to a fear, aversion, psychological hypersensitivity, or unusual intolerance of light, occurring in, for example, measles, rubella, meningitis, and inflammation of the eyes. See, Taber's Cyclopedic Medical Dictionary, 19th Ed., 2001, page 1582.

Phonophobia

The term "phonophobia" refers to a fear, aversion, psychological hypersensitivity, or dislike of sound or noise. It can refer to a fear of speaking or of hearing one's own voice. See, Taber's Cyclopedic Medical Dictionary, 19th Ed., 2001, page 1578.

Osmophobia

The term "osmophobia" refers to a fear, aversion, or psychological hypersensitivity to smells or odors. See, http://en.wikipedia.org/wiki/Osmophobia.

Allodynia

The term "allodynia" refers to a condition in which an ordinarily painless stimulus, once perceived, is experienced as being painful. See, Taber's Cyclopedic Medical Dictionary, 19th Ed., 2001, page 74.

Hyperalgesia

The term "hyperalgesia" refers to an excessive sensitivity to pain. See, Taber's Cyclopedic Medical Dictionary, 19th Ed., 2001, page 979.

Headache

The term "headache" refers to pain felt in the head region, and can include pain in the forehead, eyes, jaws, temples, scalp, skull, occiput, or neck. See, Taber's Cyclopedic Medical Dictionary, 19th Ed., 2001, page 888.

Arthritis

The term "arthritis" refers to joint inflammation, and can be accompanied by pain, swelling, stiffness, and deformity. See, Taber's Cyclopedic Medical Dictionary, 19th Ed., 2001, page 164.

Fibromyalgia

The term "fibromyalgia" refers to chronic and frequently difficult to manage pain in muscles and soft tissues surrounding joints. See, Taber's Cyclopedic Medical Dictionary, 19th Ed., 2001, page 762.

Osteoarthritis

The term "osteoarthritis" refers to a type of arthritis marked by progressive cartilage deterioration in synovial joints and vertebrae. See, Taber's Cyclopedic Medical Dictionary, 19th Ed., 2001, page 1464.

Psoriasis

The term "psoriasis" refers to a skin disorder characterized by red patches covered by thick, dry silvery adherent scales that are the result of excessive development of epithelial cells. Exacerbations and remissions can occur. See, Mosby's Medical, Nursing, & Allied Health Dictionary, 5th Ed., 1998, page 1345.

Herniated Disc

The term "herniated disc" refers to a rupture of the fibrocartilage surrounding an intervertebral disk, releasing the nucleus pulposus that cushions the vertebrae above and below. The resultant pressure on spinal nerve roots can cause pain and nerve damage. See, Mosby's Medical, Nursing, & Allied Health Dictionary, 5th Ed., 1998, page 756.

Chronic Fatigue Syndrome

The term "chronic fatigue syndrome" refers to a syndrome marked by incapacitating fatigue that rest does not relieve. It is frequently associated with decreased concentration, irritability, sleep disturbances, recurrent sore throats, low-grade temperatures, swollen glands, and bone or muscle aches. See, Taber's Cyclopedic Medical Dictionary, 19$^{th}$ Ed., 2001, page 402.

Gout: The term "gout" refers to a common group of arthritic disorders marked by the deposition of monosodium urate crystals in joints and other tissues. Any joint may be affected, but gout can sometimes begin in the knee or the first metatarsophalangeal joint of the foot. See, Taber's Cyclopedic Medical Dictionary, 19$^{th}$ Ed., 2001, page 860.

Rheumatoid Arthritis

The term "rheumatoid arthritis" refers to a destructive, inflammatory, sometimes deforming, collagen disease that has an autoimmune component. It can be characterized by symmetric inflammation of the synovium and increased synovial exudates, leading to thickening of the synovium and swelling of the joint. See, Mosby's Medical, Nursing, & Allied Health Dictionary, 5$^{th}$ Ed., 1998, page 1421.

Lupus

The term "lupus" refers to lupus erythematosus, a chronic inflammatory disease affecting many systems of the body. The pathophysiologic characteristics of the disease can include vasculitis, renal involvement, and lesions of the skin and nervous system. See, Mosby's Medical, Nursing, & Allied Health Dictionary, 5$^{th}$ Ed., a 1998, page 964, and also the definition of "systemic lupus erythematosus" at page 1582.

Multiple Sclerosis

The term "multiple sclerosis" refers to a chronic disease of the central nervous system, in which there is destruction of myelin and nerve axons within several regions of the brain and spinal cord at different times. This results in temporary, repetitive, or sustained disruptions in nerve impulse conduction, causing symptoms such as muscular weakness, numbness, visual disturbances, or loss of control of bowel, bladder, and sexual functions. See, Taber's Cyclopedic Medical Dictionary, 19$^{th}$ Ed., 2001, page 1854.

Irritable Bowel Syndrome (IBS)

The term "irritable bowel syndrome" refers to a condition marked by abdominal pain (often relieved by the passage of stool or gas); disturbances of evacuation (constipation, diarrhea, or alternating episodes of both); bloating and abdominal distention; and the passage of mucus in stools. These symptoms are present despite the absence of anatomical, biochemical, or clinical evidence of active intestinal disease. See, Taber's Cyclopedic Medical Dictionary, 19$^{th}$ Ed., 2001, page 2024.

Depression

The term "depression" refers to mood disorders marked by loss of interest or pleasure in living. Characteristic symptoms of the depressive disorders can include, for example, persistent sadness, hopelessness, or tearfulness; loss of energy (or persistent fatigue); persistent feelings of guilt or self-criticism; a sense of worthlessness; irritability; an inability to concentrate; decreased interest in daily activities; changes in appetite or body weight; insomnia or excessive sleep; and recurrent thoughts of death or suicide. These symptoms can cause pervasive deficits in social functioning. See, Taber's Cyclopedic Medical Dictionary, 19$^{th}$ Ed., 2001, page 538-539.

Anxiety

The term "anxiety" refers to a vague uneasy feeling of discomfort or dread accompanied by an autonomic response; the source is often nonspecific or unknown to the individual; a feeling apprehension caused by anticipation of danger. See, Taber's Cyclopedic Medical Dictionary, 19$^{th}$ Ed., 2001, page 137-138.

Sjögren's Syndrome

The term "Sjögren's Syndrome" refers to an autoimmune disorder marked by decreased lacrimal and salivary secretions, resulting in dry eyes and dry mouth. In Sjögren's syndrome, the lacrimal and salivary glands are destroyed by autoantibodies and T lymphocytes. In some patients it occurs alone; in others it is seen in conjunction with other autoimmune diseases, such as systemic lupus erythematosus, thyroiditis, scleroderma, and especially rheumatoid arthritis. See, Taber's Cyclopedic Medical Dictionary, 19$^{th}$ Ed., 2001, page 1901.

Ehlers-Danlos Syndrome

The term "Ehlers-Danlos Syndrome" refers to an inherited disorder of the elastic connective tissue in which the characteristic soft velvety skin is fragile, hyperelastic, and bruises easily. Symptoms can include hyperexensibility of joints, visceral malformations, atrophic scars, pseudo-tumors, and calcified subcutaneous cysts. See, Taber's Cyclopedic Medical Dictionary, 19$^{th}$ Ed., 2001, page 642.

The following is an exemplary, non-limiting list of conditions that some in the medical community believe may be related to, induced by, or caused by any part of the cascade of biochemical events included in the inflammatory response system: fibromyalgia, arthritis, osteoarthritis, herniated cervical disc, chronic fatigue syndrome, gout, rheumatoid arthritis, lupus, multiple sclerosis, neuropathic pain, irritable bowel syndrome (IBS), depression, anxiety, Sjögren's Syndrome, and Ehlers-Danlos Syndrome. Likewise, accompanying symptoms to the above conditions may be related to, induced by, or caused by any part of the cascade of biochemical events included in the inflammatory response system.

Without being bound to any particular theory of a mechanism of action, compositions of the present invention can treat conditions and/or accompanying symptoms associated with inflammation by interfering with various parts of the human inflammatory response system. For example, by interfering with the inflammatory response system at an early point in the cascade of events that give rise to inflammation, conditions and/or accompanying symptoms which are related to events that occur at any point in the biochemical process that leads to inflammation can be treated. For example, by reducing the activation of the nuclear factor NF-κB, certain embodiments can result in a decrease in pro-inflammatory cytokines/chemokines, such as, for example, TNF-α.

Sources of Extracts

Extracts of herbs consistent with the forms as set forth above can be obtained readily from multiple commercial suppliers including, for example, from Stryka Botanics, Draco Natural Products, Changsha Nutramax, BNP, and others known to one of skill in the art. Herbal extracts used in manufacturing certain prototype embodiments of the present invention were obtained from such commercial suppliers. The extract of sunflower can be obtained from Changsha Nutramax (http://www.nutra-max.com/en/main.asp) and is a standard product offering of that company. The preferred extracts of turmeric, peppermint, dandelion, ginger, feverfew, and lemon can be obtained from Draco Natural Products (http://www.dracoherbs.com) and each is a standard product offering of that company. Herbal extracts in the preferred form may also be obtained by special order from other suppliers. In the alternative, extracts can be obtained by means of common extraction procedures well known to those skilled in the art of chemistry and chemical engineering. One variation on such an extraction procedure is set forth below.

One extraction procedure can include, generally, the steps of: 1) cleaning the plant from which the pharmacologically or biologically active plant extract has to be obtained to remove any foreign matter thereon; 2) particulating the plant to obtain a particulate mass having particle size ranging from 0.001 to about 10 mm$^3$; and 3) subjecting the particulate mass to at least one polar and at least one non-polar solvent to obtain separate fractions of the plant extract soluble in the respective solvents, and mixing the fraction so obtained to obtain the beneficiated plant extract in accordance with this invention. Another specific extraction procedure includes supercritical fluid extraction (SCFE) that employs one or more solvents suitable for SCFE, at one or more temperatures and at one or more pressures, suitable to effectively extract the desired component(s) from the plant material.

Example Extraction Procedure

For example, in the case of turmeric, the process can include the steps of: 1) cleaning the rhizome of turmeric to remove any foreign matter thereon; 2) particulating the rhizome to obtain a particulate mass having particle size ranging from 0.001 to about 10 mm$^3$; 3) subjecting the particulate mass to distillation to obtain a volatile fraction, if any, from the particulate mass; 4) cooking the distilled particulate mass in a polar solvent, such as water to dissolve material in the distillation-treated particulate mass to obtain a first solution and a first residue; 5) filtering the first solution from the first residue; 6) evaporating the filtrate obtained from the first solution to remove the solvent and obtain a solute designated as fraction A from the particulated mass; 7) subjecting the first residue to treatment with a second polar solvent such as 75% to 95% ethanol for twelve to thirty-six hours to obtain a second solution and a second residue; 8) filtering the second solution from the second residue to obtain a second filtrate; 9) evaporating the second filtrate to remove its solvent and obtain a solute designated as fraction B from the particulated mass; 10) subjecting the second residue to less polar or non-polar solvents; such as petroleum ether, for twelve to thirty-six hours to obtain a third solution and a third residue, and filtering the third solution from the third residue to obtain a third filtrate; 11) evaporating the third filtrate to remove its solvent and obtain a solute designated as fraction C from the particulated mass; and 12) homogeneously mixing the volatile fraction, with fractions A, B and C from the particulated mass to obtain a beneficiated plant extract.

The process above is generally suitable for the preparation of plant extracts and can be employed generally, possibly subject to adjustments in consideration of, the concentration or extract ratio desired, any desired standardization for specific plant components (e.g. curcuminoids), the plant or plant part from which the extraction is to be obtained, and other such considerations, as known to one of skill in the art. Suitable modifications of the extraction process can be implemented, as will be immediately evident to a skilled artisan. Extracts may also be readily prepared by one of skill in the art by selecting from and in reference to one or more of the many published herbal extraction procedures.

Useful solvents for plant extractions can include water, methanol, ethanol, propanol, paraffin, hexane, petroleum ether, toluene, acetone, methyl ethyl ketone, diethyl ether, and other common organic solvents.

Water and ethanol are the most preferred solvents for preparing extracts of the active ingredients. The preferred sunflower extract, obtained from Changsha Nutramax, Inc., is reported to have been extracted using only water and ethanol as solvents in the extraction. The preferred extracts of turmeric, peppermint, dandelion, ginger, feverfew, and lemon, obtained from Draco Natural Products, Inc., are each reported to have been extracted using only water as a solvent in the extraction. In addition, each of the extracts obtained from Draco Natural Products is reported to have been extracted using "a lower temperature process," also reported as a "controlled temperature water extraction process, spray dried." Such extracts are readily available, or may be readily prepared by one skilled in the art.

Pharmaceutical Formulations

The substances present in the composition of the present invention are formulated with conventional carriers and excipients, which will be selected in accord with ordinary practice. Tablets can contain excipients, glidants, fillers, binders and the like. Aqueous formulations can be prepared in sterile form, and when intended for delivery by other than oral administration generally will be isotonic. All formulations will optionally contain excipients such as those set forth in the *Handbook of Pharmaceutical Excipients*, 5$^{th}$ Ed.; Rowe, Sheskey, and Owen, Eds.; American Pharmacists Association; Pharmaceutical Press: Washington, D.C., 2006. Excipients include ascorbic acid and other antioxidants, chelating agents such as EDTA, carbohydrates such as dextrin, hydroxyalkylcellulose, hydroxyalkylmethylcellulose, stearic acid and the like. The pH of the formulations ranges from about 3 to about 11, but is ordinarily about 7 to 10.

The formulations include those suitable for the foregoing administration routes. The formulations may conveniently be presented in unit dosage form and may be prepared by any of the methods well known in the art of pharmacy. Techniques and formulations generally are found in *Remington's Pharmaceutical Sciences*, Mack Publishing Company, Easton, Pa., (1985). Such methods include the step of bringing into association the active ingredient(s) with the carrier which constitutes one or more accessory ingredients. In general the formulations are prepared by uniformly and intimately bringing into association the active ingredient(s) with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient(s); as a powder or granules; as a solution or a suspension in an aqueous or non-aqueous liquid; or as an oil-in-water liquid emulsion or a water-in-oil liquid emulsion. The active ingredient(s) may also be administered as a bolus, electuary or paste.

A tablet is made by compression or molding, optionally with one or more accessory ingredients. Compressed tablets may be prepared by compressing in a suitable machine the active ingredient(s) in a free-flowing form such as a powder or granules, optionally mixed with a binder, lubricant, inert diluent, preservative, surface active or dispersing agent. Molded tablets may be made by molding in a suitable machine a mixture of the powdered active ingredient(s) moistened with an inert liquid diluent. The tablets may optionally be coated or scored and optionally are formulated so as to provide slow or controlled release of the active ingredient(s) therefrom.

For administration to the eye or other external tissues e.g., mouth and skin, the formulations are preferably applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredient(s) may be employed with either a paraffinic or a water-miscible ointment base. Alternatively, the active ingredient(s) may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient(s) through the skin or other affected areas. Examples of such dermal penetration enhancers include dimethyl sulphoxide and related analogs.

The oily phase of the emulsions of the present invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the present invention include Tween® 60, Span® 80, cetostearyl alcohol, benzyl alcohol, myristyl alcohol, glyceryl mono-stearate and sodium lauryl sulfate.

The choice of suitable oils or fats for the formulation is based on achieving the desired properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Pharmaceutical formulations according to the present invention include one or more substances described herein, together with one or more pharmaceutically acceptable carriers or excipients and optionally other therapeutic agents. Pharmaceutical formulations containing the active ingredient(s) may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient(s) in admixture with non-toxic pharmaceutically acceptable excipient which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient(s) is mixed with an inert solid diluent, for example calcium phosphate or kaolin, or as soft gelatin capsules wherein the active ingredient(s) is mixed with water or an oil medium, such as peanut oil, liquid paraffin or olive oil.

Aqueous suspensions of the present invention contain the active materials in admixture with excipients suitable for the manufacture of aqueous suspensions. Such excipients include a suspending agent, such as sodium carboxymethylcellulose, methylcellulose, hydroxypropyl methylcelluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

Oil suspensions may be formulated by suspending the active ingredient(s) in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the present invention suitable for preparation of an aqueous suspension by the addition of water provide the active ingredient(s) in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the present invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

The pharmaceutical compositions of the present invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient(s) that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 µg of the active ingredient(s) per milliliter of solution in order that infusion of a suitable volume at a rate of about 30 mL/hr can occur.

Formulations suitable for administration to the eye include eye drops wherein the active ingredient(s) is dissolved or suspended in a suitable carrier, especially an aqueous solvent for the active ingredient(s). The active ingredient(s) is preferably present in such formulations in a concentration of 0.5 to 20%, advantageously 0.5 to 10% particularly about 1.5% w/w.

Formulations suitable for topical administration in the mouth include lozenges comprising the active ingredient(s) in a flavored basis, usually sucrose and acacia or tragacanth; pastilles comprising the active ingredient(s) in an inert basis such as gelatin and glycerin, or sucrose and acacia; and mouthwashes comprising the active ingredient(s) in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient(s). Formulations suitable for aerosol or dry powder administration may be prepared according to conventional methods and may be delivered with other therapeutic agents such as compounds heretofore used in the treatment or prophylaxis of a given condition.

Formulations suitable for vaginal administration may be presented as pessaries, tampons, creams, gels, pastes, foams or spray formulations containing in addition to the active ingredient(s) such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient(s).

It should be understood that in addition to the ingredients particularly mentioned above the formulations of this present invention may include other agents conventional in the art having regard to the type of formulation in question, for example those suitable for oral administration may include flavoring agents.

The present invention further provides veterinary compositions comprising at least one active ingredient(s) as above defined together with a veterinary carrier therefor.

Veterinary carriers are materials useful for the purpose of administering the composition and may be solid, liquid or gaseous materials which are otherwise inert or acceptable in the veterinary art and are compatible with the active ingredient(s). These veterinary compositions may be administered orally, parenterally or by any other desired route.

The compositions of the present invention can also be formulated to provide controlled release of the active ingredient(s) to allow less frequent dosing or to improve the pharmacokinetic or toxicity profile of the active ingredient(s). Accordingly, the present invention also provides compositions that include one or more compositions of the present invention formulated for sustained or controlled release.

Effective dose of active ingredient(s) depends at least on the nature of the condition being treated, toxicity, whether the compound is being used prophylactically (lower doses), the method of delivery, and the pharmaceutical formulation, and will be determined by the clinician using conventional dose escalation studies. It can be expected to be from about 0.0001 to about 100 mg/kg body weight per day. Typically, from about 0.01 to about 10 mg/kg body weight per day. More typically, from about 0.01 to about 5 mg/kg body weight per day. More typically, from about 0.05 to about 0.5 mg/kg body weight per day. For example, the daily candidate dose for an adult human of approximately 70 kg body weight will range from 1 mg to 1000 mg, preferably between 5 mg and 500 mg, and may take the form of single or multiple doses.

Routes of Administration

One or more compositions of the present invention are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compositions of the present invention is that they are orally bioavailable and can be conveniently dosed orally.

The present invention can now be illustrated by the following non-limiting embodiments.

Embodiments

[1] The present invention provides for a pharmaceutical composition comprising a pharmaceutically acceptable carrier and at least two of:

(a) sunflower extract,
(b) rhubarb root extract,
(c) milk thistle extract,
(d) dandelion extract,
(e) feverfew extract, and
(f) ginger extract.

[2] The present invention also provides for a pharmaceutical composition of embodiment [1], comprising at least three of (a)-(f).

[3] The present invention also provides for a pharmaceutical composition of embodiment [1], comprising at least four of (a)-(f).

[4] The present invention also provides for a pharmaceutical composition of embodiment [1], comprising at least five of (a)-(f).

[5] The present invention also provides for a pharmaceutical composition of embodiment [1], comprising each of (a)-(f).

[6] The present invention also provides for a pharmaceutical composition of any one of embodiments [1]-[5], wherein the sunflower extract is present in about 1 wt. % to about 10 wt. % of the composition.

[7] The present invention also provides for a pharmaceutical composition of any one of embodiments [1]-[6], wherein the rhubarb root extract is present in about 0.5 wt. % to about 5 wt. % of the composition.

[8] The present invention also provides for a pharmaceutical composition of any one of embodiments [1]-[7], wherein the milk thistle extract is present in about 0.5 wt. % to about 5 wt. % of the composition.

[9] The present invention also provides for a pharmaceutical composition of any one of embodiments [1]-[8], wherein the dandelion extract is present in about 0.1 wt. % to about 3 wt. % of the composition.

[10] The present invention also provides for a pharmaceutical composition of any one of embodiments [1]-[9], wherein the feverfew extract is present in about 0.1 wt. % to about 3 wt. % of the composition.

[11] The present invention also provides for a pharmaceutical composition of any one of embodiments [1]-[10], wherein the ginger extract is present in about 0.1 wt. % to about 3 wt. % of the composition.

[12] The present invention also provides for a pharmaceutical composition of any one of embodiments [1]-[11], further comprising lemon extract.

[13] The present invention also provides for a pharmaceutical composition of any one of embodiments [1]-[11], further comprising lemon extract present in about 1 wt. % to about 15 wt. % of the composition.

[14] The present invention also provides for a pharmaceutical composition of any one of embodiments [1]-[13], further comprising peppermint extract.

[15] The present invention also provides for a pharmaceutical composition of any one of embodiments [1]-[13], further comprising peppermint extract present in about 0.1 wt. % to about 5 wt. % of the composition.

[16] The present invention also provides for a pharmaceutical composition of any one of embodiments [1]-[15], further comprising turmeric extract.

[17] The present invention also provides for a pharmaceutical composition of any one of embodiments [1]-[16], further comprising rebiana.

[18] The present invention also provides for a pharmaceutical composition of any one of embodiments [1]-[17], further comprising cellulose.

[19] The present invention also provides for a pharmaceutical composition of any one of embodiments [1]-[18], further comprising corn starch.

[20] The present invention also provides for a pharmaceutical composition of any one of embodiments [1]-[19], further comprising citric acid.

[21] The present invention also provides for a pharmaceutical composition of any one of embodiments [1]-[20], further comprising dextrose.

[22] The present invention also provides for a pharmaceutical composition of any one of embodiments [1]-[21], further comprising magnesium stearate.

[23] The present invention also provides for a pharmaceutical composition of any one of embodiments [1]-[22], further comprising at least one of an:
(a) adsorbent,
(b) suspending agent,
(c) diluent,
(d) disintegrant,
(e) glidant,
(f) binder,
(g) acidifying agent,
(h) basifying agent,
(i) antioxidant,
(j) buffering agent,
(k) chelating agent,
(l) flavor enhancer,
(m) tonicity agent,
(n) sweetening agent,
(o) lubricant,
(p) flavoring agent,
(q) coloring agent,
(r) dye, and
(s) penetration enhancer.

[24] The present invention also provides for a pharmaceutical composition comprising:
(a) lemon extract,
(b) sunflower extract,
(c) rhubarb root extract,
(d) milk thistle extract,
(e) dandelion extract,
(f) feverfew extract,
(g) ginger extract,
(h) cellulose,
(i) citric acid,
(j) corn starch,
(k) dextrose,
(l) magnesium stearate,
(m) peppermint extract,
(n) rebiana, and
(o) turmeric extract.

[25] The present invention also provides for a pharmaceutical composition of any one of embodiments [1]-[24], that is suitable for oral administration.

[26] The present invention also provides for a pharmaceutical composition of any one of embodiments [1]-[24], that is suitable for transmucosal administration.

[27] The present invention also provides for a pharmaceutical composition of any one of embodiments [1]-[24], that is an oral tablet, lozenge or troche.

[28] The present invention also provides for a pharmaceutical composition of any one of embodiments [1]-[24], that is an oral tablet, lozenge or troche having a mass of at least about 0.5 gram.

[29] The present invention also provides for the pharmaceutical composition in any one of embodiments [1]-[28], for use in medical therapy.

[30] The present invention also provides for the pharmaceutical composition in any one of embodiments [1]-[28], to prepare a medicament for providing symptomatic relief to a human afflicted with inflammation.

[31] The present invention also provides for a method for providing symptomatic relief to a human afflicted with inflammation, the method comprising administering to a patient in need of such symptomatic relief an effective amount of the pharmaceutical composition of any one of embodiments [1]-[28], for a period of time sufficient to provide symptomatic relief to the human.

[32] The present invention also provides for the pharmaceutical composition of embodiment [29], the method of embodiment [30], or the method of embodiment [31], wherein the administration is systemic.

[33] The present invention also provides for the pharmaceutical composition of embodiment [29], the method of embodiment [30], or the method of embodiment [31], wherein the administration is a transmucosal administration.

[34] The present invention also provides for the pharmaceutical composition of embodiment [29], the method of embodiment [30], or the method of embodiment [31], wherein the administration is a transmucosal administration, via the mucosal membrane of the mouth.

[35] The present invention also provides for the pharmaceutical composition of any one of embodiments [32]-[34] or the method of any one of embodiments [32]-[34], wherein the administration occurs over a period of time of at least about 2 minutes.

[36] The present invention also provides for the pharmaceutical composition of any one of embodiments [32]-[35] or the method of any one of embodiments [32]-[35], wherein the pharmaceutical composition is administered at least about once per day.

[37] The present invention also provides for the pharmaceutical composition of any one of embodiments [32]-[36] or the method of any one of embodiments [32]-[36], wherein the pharmaceutical composition is administered over a period of time of at least about 1 week.

[38] The present invention also provides for the pharmaceutical composition of any one of embodiments [32]-[37] or the method of any one of embodiments [32]-[37], wherein the symptom associated with inflammation comprises at least one of psoriasis, diffuse pain, jaw or facial pain, back or neck pain, muscle pain, joint pain, arthritis pain, osteoarthritis pain, pelvic pain, chest pain, neuropathic pain, vulvodynia, urethral pain, weakness, fatigue, chronic fatigue, dizziness, paresthesia, impaired cognition, sleep disturbance, joint stiffness, tendonitis, hypersensitivity to cold, hypersensitivity to sensory stimuli, photophobia, phonophobia, osmophobia, allodynia, hyperalgesia, and headache.

[39] The present invention also provides for the pharmaceutical composition of any one of embodiments [32]-[38] or the method of any one of embodiments [32]-[38], wherein the inflammation is associated with at least one of arthritis, fibromyalgia, osteoarthritis, herniated cervical disc, chronic fatigue syndrome, gout, rheumatoid arthritis, lupus, multiple sclerosis, neuropathic pain, irritable bowel syndrome (IBS), depression, anxiety, Sjögren's Syndrome, and Ehlers-Danlos Syndrome.

The present invention can now be illustrated by the following non-limiting examples.

EXAMPLES

Example 1

Thirty-two individuals with doctor-diagnosed fibromyalgia participated in a study to test the effectiveness of an embodiment of the present invention. The participants used a lozenge of the present invention twice a day for 29 days, in the morning and in the evening, by allowing the lozenge to dissolve in the mouth. The 1 g lozenge included about 2.5 wt. % sunflower seed extract, about 0.75 wt. % dandelion extract, 0.1 wt. % feverfew extract, 0.5 wt. % ginger extract, 5 wt. % lemon extract, 1 wt. % peppermint extract, and 5 wt. % turmeric extract. The participants ranged from 24 to 74 years of age, with an average age of 46, and reported having had fibromyalgia for between 2 and 30 years with an average of 11 years.

At the beginning and end of the study, the participants were asked to rate the frequency and severity of their symptoms. They were also asked to rate their general level of pain, fatigue, and sleep impairment. A comparison between the ratings at the beginning and end of the study are shown below. Most participants achieved a substantial reduction in both the severity and frequency of multiple symptoms after 29 days of treatment.

|  | 29 DAYS | | |
| --- | --- | --- | --- |
| Global Assessment | Average percent improvement | Percent reporting improvement | Percent with ≥50% improvement |
| Overall Pain | 25 | 69 | 31 |
| Fatigue | 25 | 72 | 22 |
| Impaired Sleep | 29 | 69 | 31 |

| Individual Symptoms | Freq | Sever | Freq | Sever | Freq | Sever |
| --- | --- | --- | --- | --- | --- | --- |
| Diffuse Pain | 49 | 44 | 69 | 65 | 50 | 53 |
| Joint Pain | 44 | 40 | 64 | 68 | 45 | 32 |
| Back/Neck Pain | 35 | 30 | 58 | 50 | 41 | 28 |
| Jaw/Facial Pain | 39 | 43 | 67 | 57 | 54 | 46 |
| Stiffness | 39 | 35 | 69 | 65 | 38 | 34 |
| Odd Skin Sensation | 42 | 44 | 64 | 64 | 59 | 48 |
| Post-Exer. Fatigue | 35 | 30 | 46 | 58 | 31 | 34 |
| All-day Fatigue | 53 | 40 | 72 | 68 | 48 | 35 |
| "Fibro-fog" | 41 | 33 | 65 | 50 | 63 | 53 |
| Headaches | 43 | 43 | 65 | 57 | 57 | 54 |
| Insomnia | 41 | 44 | 65 | 69 | 61 | 55 |
| Depression | 51 | 43 | 77 | 77 | 56 | 67 |
| Anxiety | 59 | 50 | 76 | 76 | 65 | 69 |

Example 2

Of the thirty-two participants of Example 1, eighteen reported having chronic fatigue syndrome (CFS). Of the participants having CFS, most reported having an improvement in CFS symptoms such as sleep reduction and fatigue reduction after the 29 day study.

|  | Herbal Lozenge: % achieving | Herbal Lozenge: % achieving |
| --- | --- | --- |
| Sleep | | |
| Any (>0%) | 69 | 61 |
| ≥15% | 63 | 50 |
| ≥30% | 44 | 33 |
| ≥50% | 31 | 22 |
| ≥70% | 13 | 6 |
| Fatigue Reduction | | |
| Any (>0%) | 72 | 56 |
| ≥15% | 63 | 44 |
| ≥30% | 44 | 33 |

|  | Herbal Lozenge: % achieving | Herbal Lozenge: % achieving |
|---|---|---|
| ≥50% | 22 | 11 |
| ≥70% | 9 | 6 |

Example 3

Of the thirty-two participants of Example 1, eleven reported having osteoarthritis. Of the participants having osteoarthritis, most reported having an improvement in osteoarthritis symptoms such as joint pain after the 29 day study.

| Joint Pain | Frequency | Severity |
|---|---|---|
| Initial Average | 6.5 | 2.5 |
| After 14 days | | |
| Average reduction (% reduction) | 2.2 (34%) | 0.8 (33%) |
| Percent reporting reduction | 55% | 64% |
| Percent with ≥50% reduction | 45% | 27% |
| After 29 days | | |
| Average reduction (% reduction) | 2.4 (37%) | 0.8 (33%) |
| Percent reporting reduction | 55% | 73% |
| Percent with ≥50% reduction | 55% | 36% |

Example 4

Of the thirty-two participants of Example 1, five reported having rheumatoid arthritis. Of the five participants having rheumatoid arthritis, after the 29 day study two individuals reported no reduction in joint paint, two individuals reported at least a 30% reduction in joint pain, and one individual reported at least a 50% reduction in joint pain.

Example 5

Of the thirty-two participants of Example 1, seventeen reported having migraines. Of the seventeen participants having migraines, most reported having an improvement in migraine symptoms such as headache after the 29 day study.

| Headache | Frequency Only Migraine | Severity Only Migraine |
|---|---|---|
| Initial Average | 4.4 | 2.3 |
| After 14 days | | |
| Average reduction (% reduction) | 2.2 (49%) | 1.2 (51%) |
| Percent reporting reduction | 76% | 76% |
| Percent with ≥50% reduction | 47% | 65% |

| Headache | Frequency Only Migraine | Severity Only Migraine |
|---|---|---|
| After 29 days | | |
| Average reduction (% reduction) | 1.5 (33%) | 0.9 (41%) |
| Percent reporting reduction | 59% | 59% |
| Percent with ≥50% reduction | 47% | 47% |

Example 6

Seven individuals with doctor-diagnosed fibromyalgia participated in a study to test the effectiveness of an embodiment of the present invention. The participants used a lozenge of the present invention twice a day for 10 days, in the morning and in the evening, by allowing the lozenge to dissolve in the mouth. The 4.0 g lozenge included about 2.5 wt. % sunflower seed extract, about 0.75 wt. % dandelion extract, 0.1 wt. % feverfew extract, 0.5 wt. % ginger extract, 5 wt. % lemon extract, 1 wt. % peppermint extract, and 5 wt. % turmeric extract. The participants ranged from 25 to 56 years of age, with an average age of 43, and reported having had fibromyalgia for between 4.5 and 30 years with an average of 10.5 years.

At the beginning and end of the study, the participants were asked to rate their general level of pain, fatigue, and sleep impairment. A comparison between the ratings at the beginning and end of the study are shown below.

| | 10 DAYS | | |
|---|---|---|---|
| Global Assessment | Average percent improvement | Percent reporting improvement | Percent with ≥50% improvement |
| Pain | 25 | 43 | 29 |
| Fatigue | 31 | 86 | 14 |
| Impaired Sleep | 47 | 86 | 57 |

The invention claimed is:

1. A method for treating a condition selected from the group consisting of arthritis, fibromyalgia, osteoarthritis, herniated cervical disc, chronic fatigue syndrome, gout, rheumatoid arthritis, lupus, multiple sclerosis, neuropathic pain, irritable bowel syndrome, Sjogren's Syndrome and Ehlers-Danlo's Syndrome consisting essentially of administering therapeutically effective amounts of a sunflower extract, a milk thistle extract, a dandelion extract, a feverfew extract and a ginger extract to a human in need thereof to treat said condition.

* * * * *

UNITED STATES PATENT AND TRADEMARK OFFICE
CERTIFICATE OF CORRECTION

PATENT NO.       : 8,609,156 B2
APPLICATION NO. : 13/500504
DATED            : December 17, 2013
INVENTOR(S)      : Stephen Charles Roberts It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 14 days.

Signed and Sealed this
Twenty-second Day of September, 2015

Michelle K. Lee
*Director of the United States Patent and Trademark Office*